(12) United States Patent
Ardizzone et al.

(10) Patent No.: US 6,939,287 B1
(45) Date of Patent: *Sep. 6, 2005

(54) MAGNETOTHERAPEUTIC DEVICE WITH BIO-CERAMIC FIBERS

(75) Inventors: Vincent Ardizzone, Port Jefferson, NY (US); Anthony Bove, Port Jefferson, NY (US)

(73) Assignee: Nu-Magnetics, Inc., Port Jefferson, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/674,687

(22) Filed: Sep. 30, 2003

Related U.S. Application Data (63) Continuation-in-part of application No. 09/992,702, filed on Nov. 14, 2001, now abandoned, which is a continuation of application No. 09/616,751, filed on Jul. 14, 2000, now Pat. No. 6,383,129, and a continuation-in-part of application No. 09/909,674, filed on Jul. 19, 2001, now Pat. No. 6,652,446.

(60) Provisional application No. 60/143,809, filed on Jul. 14, 1999.

(51) Int. Cl.$^7$ .............................................. A61N 1/00
(52) U.S. Cl. ........................................... 600/9; 600/15
(58) Field of Search ..................................... 600/9–15

(56) References Cited

U.S. PATENT DOCUMENTS

| | | | |
|---|---|---|---|
| 3,483,494 A | 12/1969 | Cromie | 335/303 |
| 3,546,643 A | 12/1970 | Virostek | 335/303 |
| 3,885,383 A | 5/1975 | Tanaka | |
| 3,921,620 A | 11/1975 | Nakayama | 600/15 |
| 4,162,672 A | 7/1979 | Yazaki | 128/1.3 |
| 4,186,729 A | 2/1980 | Harrison | 600/15 |
| 4,374,516 A | 2/1983 | Harrison | 600/15 |
| 4,391,270 A | 7/1983 | Uragami | 600/15 |
| 4,480,596 A | 11/1984 | Shumiyashu | 600/15 |
| 4,489,711 A | 12/1984 | Latzke | 600/15 |

(Continued)

FOREIGN PATENT DOCUMENTS

| | | |
|---|---|---|
| AU | 424257 | 9/1970 |

(Continued)

*Primary Examiner*—John P. Lacyk
(74) *Attorney, Agent, or Firm*—Daniel M. Cislo (57) ABSTRACT

A magnetotherapeutic device incorporates bio-ceramic fibers so as to provide simultaneous magnetotherapy and far infra-red wave therapy. Generally encased in clear plastic or the like, the magnetotherapeutic device of the present invention may take the form of a transparent disk having a plastic rim. A stainless cap may provide an attractive top surface into which a logo or symbol may be embossed. It also enhances the magnetic affects on the side opposite the stainless steel cap, the side that is applied to the body. A strong magnet such as one incorporating neodymium may underlie the stainless steel cap to provide magnetotherapy in the present invention. Bio-ceramic fibers emitting the far infra-red wavelengths of 8–14 microns underlie the strong neodymium magnet. A mat of woven bio-ceramic fibers or the like may provide such a structure. In order to provide ventilation and communication between the environment outside of the magnetotherapeutic device of the present invention, perforated or foramenous MYLAR may serve as a bottom cover encasing the stainless steel cap, neodymium magnet, bio-ceramic fibers, and the plastic case. The perforated or foramenous MYLAR may then provide better communication between the thermal radiation of the adjacent body and emittance of far infra-red waves by the bio-ceramic fibers.

22 Claims, 7 Drawing Sheets

U.S. PATENT DOCUMENTS

| | | | | |
|---|---|---|---|---|
| 4,549,532 | A | 10/1985 | Baermann | 600/15 |
| 4,886,972 | A | 12/1989 | Nakai et al. | 250/504 R |
| 4,925,134 | A | 5/1990 | Keller et al. | 244/158 A |
| 5,017,185 | A | 5/1991 | Baermann | 600/10 |
| 5,055,189 | A | 10/1991 | Ito | 210/222 |
| 5,122,291 | A | 6/1992 | Wolff et al. | 252/62 |
| 5,138,133 | A | 8/1992 | Sakurada et al. | 219/211 |
| 5,161,272 | A | 11/1992 | Yamaguchi et al. | 600/9 |
| 5,277,692 | A | 1/1994 | Ardizzone | 600/9 |
| 5,304,111 | A | 4/1994 | Mitsuno et al. | 600/9 |
| 5,451,199 | A | 9/1995 | Kim et al. | 600/9 |
| 5,514,072 | A | 5/1996 | Ardizzone | 600/9 |
| 5,538,495 | A | 7/1996 | Ardizzone | 600/9 |
| 5,567,891 | A | 10/1996 | Bogatin et al. | 75/244 |
| 5,601,909 | A | 2/1997 | Kubo | 442/417 |
| 5,626,951 | A | 5/1997 | Hogenson | 442/262 |
| 5,628,900 | A | 5/1997 | Naito | 210/223 |
| 5,738,624 | A | 4/1998 | Zablotsky et al. | 600/9 |
| 5,769,971 | A | 6/1998 | Kuroda et al. | 420/434 |
| 5,788,624 | A | 8/1998 | Lu et al. | 600/9 |
| 5,792,176 | A | 8/1998 | Chang | 606/204 |
| 5,800,905 | A | 9/1998 | Sheridan et al. | 428/157 |
| 5,807,233 | A | 9/1998 | Sakuma et al. | 600/15 |
| 5,811,168 | A | 9/1998 | Rasky et al. | 428/102 |
| 5,871,438 | A | 2/1999 | Ardizzone | 600/9 |
| 5,891,331 | A | 4/1999 | Yang | 210/222 |
| 5,894,067 | A | 4/1999 | Kim | 501/128 |
| 5,984,856 | A | 11/1999 | Love | 600/15 |
| 5,989,178 | A * | 11/1999 | Chiu | 600/15 |
| 6,328,684 | B1 | 12/2001 | Ardizzone | 600/9 |
| 6,383,129 | B1 * | 5/2002 | Ardizzone et al. | 600/9 |

FOREIGN PATENT DOCUMENTS

| | | |
|---|---|---|
| EP | 0081109 | 6/1983 |
| FR | 1215110 | 5/1960 |
| FR | 2371916 | 11/1976 |
| GB | 2196855 A | 5/1988 |
| JP | 56-7405 | 1/1981 |

* cited by examiner

FIG. 5

|   |   |   |   |   |
|---|---|---|---|---|
| N | S | N | S | N |
| S | N | S | N | S |
| N | S | N | S | N |
| S | N | S | N | S |
| N | S | N | S | N |

MAGNETOTHERAPEUTIC DEVICE WITH BIO-CERAMIC FIBERS

CROSS-REFERENCES TO RELATED APPLICATIONS

This application is a continuation-in-part of U.S. patent application Ser. No. 09/992,702 filed Nov. 14, 2001 now abandoned which is a continuation of U.S. patent application Ser. No. 09/616,751 filed Jul. 14, 2000 and which issued as U.S. Pat. No. 6,383,129, which is related to issued to U.S. Provisional Patent Application Ser. No. 60/143,809 filed on Jul. 14, 1999. This application is also a continuation-in-part of U.S. patent application Ser. No. 09/909,674 filed on Jul. 19, 2001 now U.S. Pat. No. 6,652,446 entitled Deep Heating Magnetic Wrap for Joints and Tissue. The aforementioned applications are all hereby incorporated by reference.

COPYRIGHT AUTHORIZATION

Portions of the disclosure of this patent document may contain material which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

BACKGROUND OF THE INVENTION

1. Field of the Invention

This invention relates to magnetotherapeutic devices, and more particularly to a magnetotherapeutic device in the form of a disk or otherwise that is used in conjunction with bio-ceramic fibers to provide magnetotherapy and far infra-red treatment.

2. Description of the Related Art

Magnetotherapy is known in the art and used to provide relief for aches and pains by the application of magnetics, particularly strong magnets, to the affected area of the body. Due to the Hall effect and otherwise, the travel of fluids in the body past areas influenced by the magnetotherapeutic magnet or subject to magnetotherapy causes charges, such as those in electrolytes, to undergo forces and gently churn the fluids (such as blood, lymph, and plasma) in which they travel. Such innate activity of the bodily fluids may serve to stimulate a number of body processes.

Recent developments in the art have found that human tissue is advantageously susceptible to light in the far infra-red range. Infra-red light waves are generally known as heat waves and serve to warm objects thermally upon which such infra-red waves come into contact or shine upon. Light waves in the far infra-red may have a tendency to penetrate more deeply into the tissue and serve to stimulate such tissue accordingly.

The present invention provides means by which such effects may be combined into a conveniently applied unit, such that fluids coursing through the body may be stimulated by magnetotherapy while the deeper tissues of the body may be subject to far infra-red stimulation in combination with such magnetotherapy.

SUMMARY OF THE INVENTION

The present invention provides a magnetotherapeutic device, such as one in the shape of a disk, that uses a strong neodymium (periodic element symbol Nd) to provide magnetotherapy to tissues adjacent the magnet. Additionally, such magnetotherapy is provided in conjunction with tissue treatment by far infra-red waves as bio-ceramic fibers are provided in conjunction with the supplied magnetotherapy.

Bio-ceramic fibers are able to radiate or provide far infra-red waves at room temperature and when heated to a body temperature of approximately 98.6° F. As magnetotherapy requires the application of the magnetism to tissue, by holding the present invention as a magnetotherapeutic device against the body, the accompanying bio-ceramic fibers allow the device to provide both magnetotherapy and far infra-red treatment to the adjacent tissue.

In order to provide a convenient and integral system, a plastic case circumscribes the entire manufacture. The plastic case may provide thermal, electrical and/or other insulation, operating as an insulator or otherwise. The bio-ceramic fibers are provided in the form of a mat covered with a perforated or foramenous MYLAR cover. Backing the bio-ceramic fiber mat may be the neodymium (Nd) or other strong magnet.

In order to provide a convenient and integral system, a plastic case circumscribes the entire manufacture. The bio-ceramic fibers are provided in the form of a mat covered with a perforated or foramenous MYLAR polyester or other plastic or resilient cover. Backing the bio-ceramic fiber mat may be the neodymium (Nd) or other strong magnet.

The neodymium magnet is such that it is very difficult to lift off a ferromagnetic surface such as a filing cabinet or otherwise. The strong magnet is backed with stainless steel or other similar material which reduces the magnetic effect of the strong magnet on the side opposite the bio-ceramic fiber mat and the perforated MYLAR cover. Indicia may be provided such as embossment of the stainless steel cover and the entirety of the manufacture may be encased in plastic. The stainless steel cover may augment the magnetic field on the opposite, or bio-ceramic, side of the magnet.

The perforations or openings present in the MYLAR cover of the bio-ceramic fiber mat serve to allow quicker warming by the body of the bio-ceramic fiber mat so that it may more quickly provide far infra-red treatment. It also provides unobstructed transmission of such far infra-red waves from the fibers adjacent the perforation holes.

OBJECTS OF THE INVENTION

It is an object of the present invention to provide magnetotherapy in conjunction with far infra-red treatment of body tissues.

It is another object of the present invention to provide such magnetotherapy by means of a strong magnet.

It is yet another object of the present invention to provide such far infra-red treatment by providing bio-ceramic fibers that radiate, transmit, emit, or provide far infra-red waves at least when brought to body temperature.

It is yet another object of the present invention to combine magnetotherapy and far infra-red wave treatment in an integral and consolidated device that is convenient to apply and use.

These and other objects of and advantages of the present invention will be apparent from a review of the following specification and accompanying drawings.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
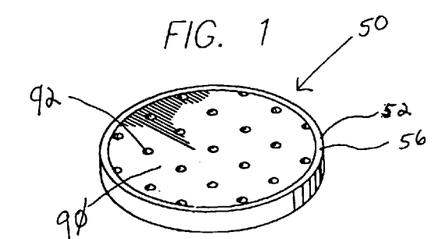
FIG. 1 is a side top perspective view of the bottom side of the magnetic disk embodiment of the present invention showing the bio-ceramic fibers covered by the perforated or foramenous MYLAR cover, all held in place by the circumscribing plastic rim of the disk.
Figure 2:
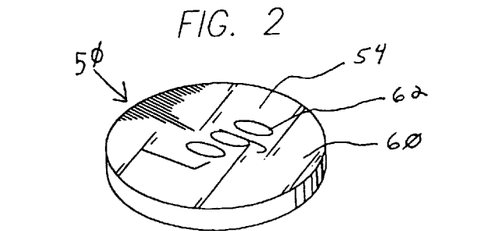
FIG. 2 is a top left side perspective view of the magnetic disk embodiment of FIG. 1 showing the stainless steel top.
Figure 3:
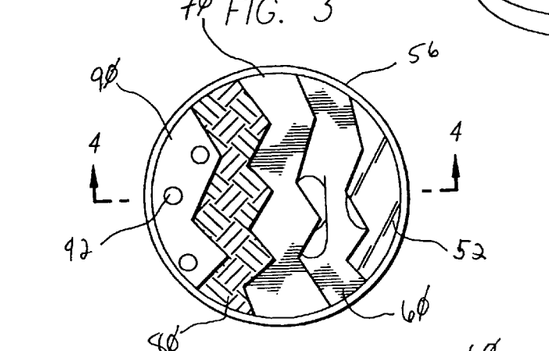
FIG. 3 shows a top cutaway sectional view of the magnetotherapeutic and far infra-red wave disk of FIGS. 1 and 2.
Figure 4:
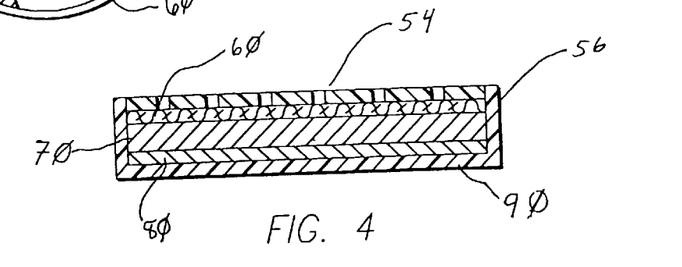
FIG. 4 shows a side cross sectional view of the disk of FIG. 3.
Figure 5:
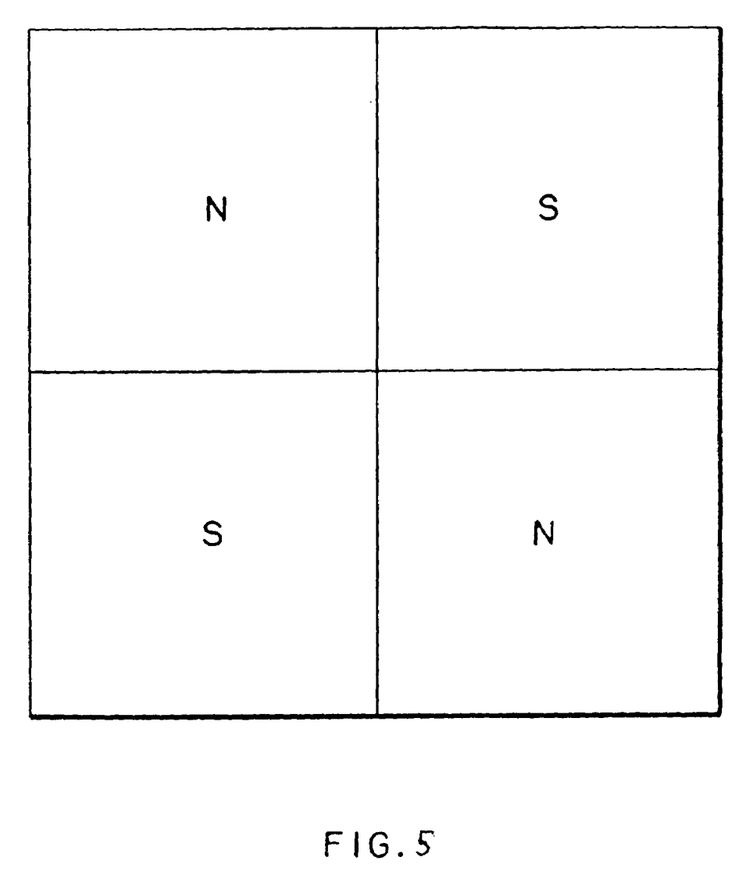
FIGS. 5 and 6 show a checkerboard-type magnet configuration for use in the present invention.
Figure 6:
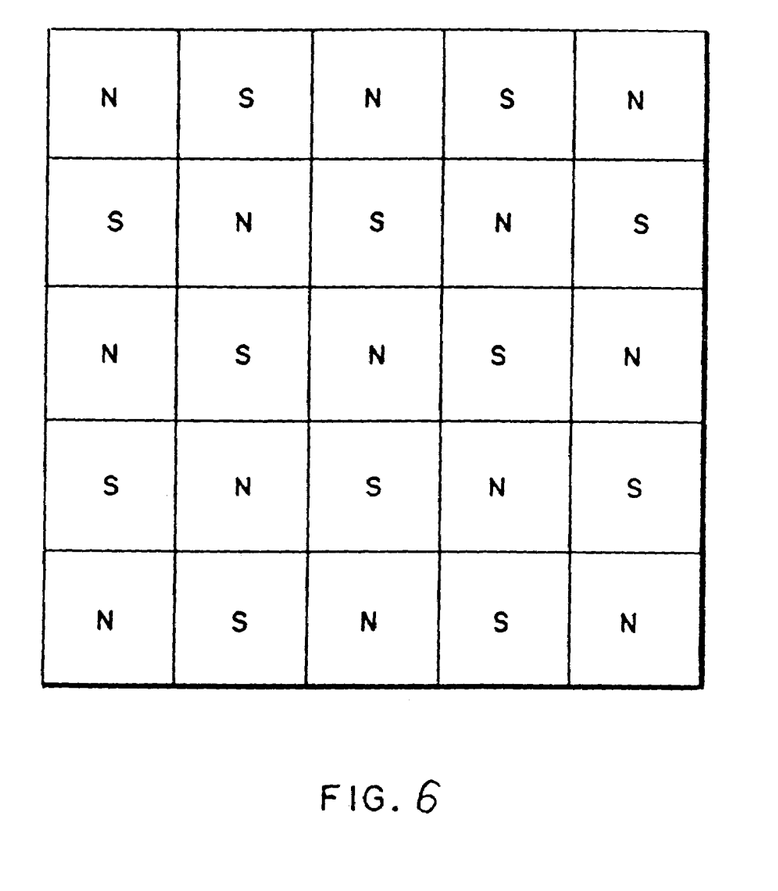
Figure 7:
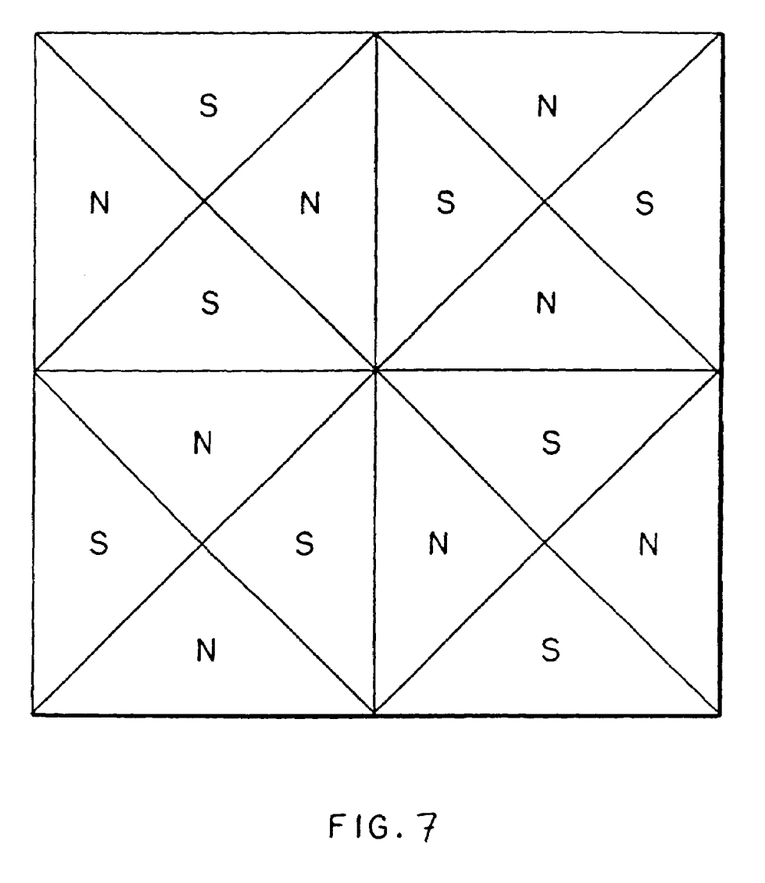
FIGS. 7 and 8 show a triangular checkerboard magnet configuration for use in the present invention.
Figure 8:
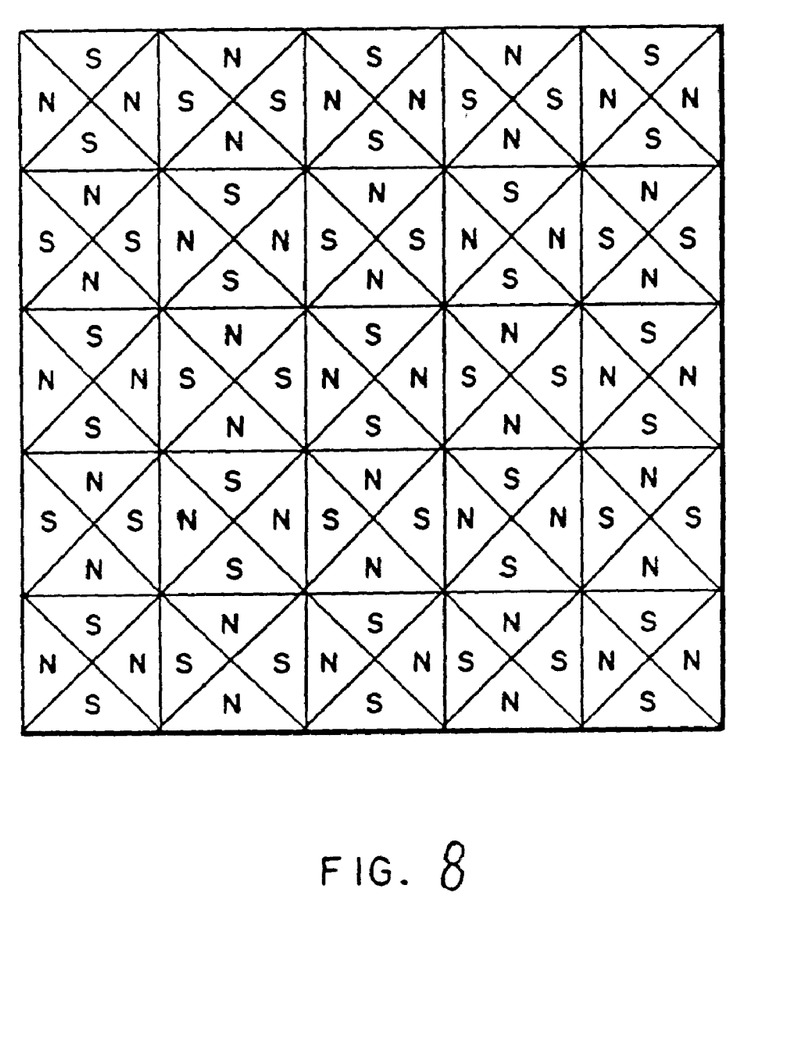
Figure 9:
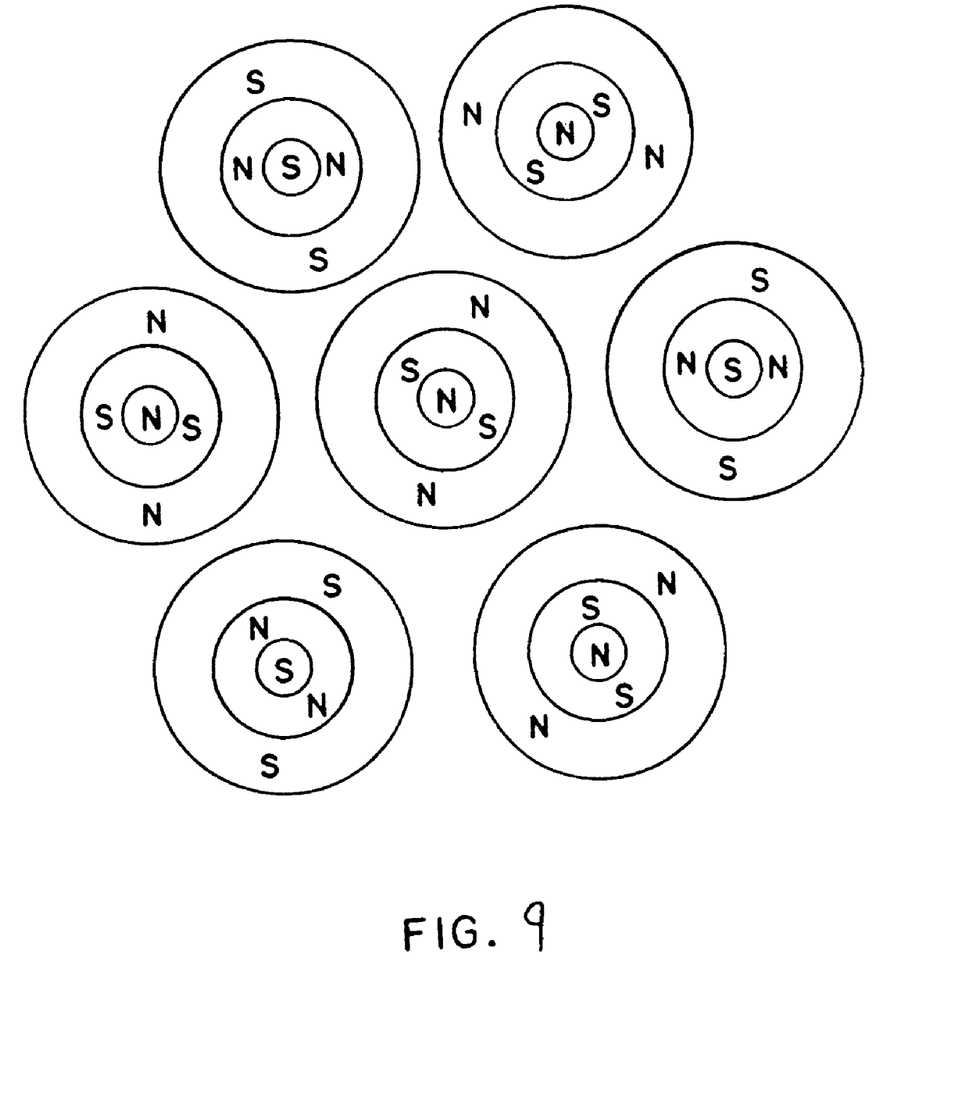
FIG. 9 shows a circular and toroidal magnet configuration for use in the present invention.

Referring to the drawings where like numerals of reference designate like elements throughout it will be noted that the figures show different views of the magnetotherapeutic and bio-ceramic (far infra-red wave) device. The embodiments shown in the drawings are ones of a disk; however, other geometrical shapes may also advantageously implement the present invention. As shown in FIGS. 1 and 3, the magnetotherapeutic device of the present invention 50 has a plastic case 52 which covers the top 54. The plastic case 52 may provide thermal, electrical and/or other insulation, operating as an insulator or otherwise. The plastic case 52 also forms a rim 56 circumscribing the device 50. In the Figures, the device 50 is shown in the shape of a disk.

The Figures show different views of the magnetotherapeutic and bio-ceramic (far infra-red wave) device. The embodiments shown in the drawings are ones of a disk; however, other geometrical shapes may also advantageously implement the present invention. As shown in FIGS. 1 and 3, the magnetotherapeutic device of the present invention 50 has a plastic ase 52 which covers the top 54. The plastic case 52 also forms a rim 56 circumscribing the device 50. In the Figures, the device 50 is shown in the shape of a disk.

A stainless steel top cover 60 may be embossed with a figure or emblem 62. The stainless steel top 60 also serves to limit or diminish the magnetic field generated by the strong magnet 70 past the top 54, but may serve to augment the magnetic field below it.

The strong magnet 70 may also be in the shape of a disk and preferably so in the embodiments shown in the Figures. The strong magnet 70 provides the magnetotherapy present in the present invention. The magnet 70 may be made of neodymium (Nd) or the like or any other strong magnet that is currently available or developed in the future that is safe and non-toxic.

Below the magnet 70 is a woven mat or other structure of bio-ceramic fibers 80 such as those marketed by 3M™ under the Nextel™ trademark. As shown in the accompanying Exhibit, the Nextel™ 312 fabric provides good far infrared (FIR) emittance in the 8–14 micron wavelength range. From the Exhibit, the Nextel™ 312 fabric is made up of crystals less than 500 nanometers large of $9Al_2O_3$: $2B_2O_3$+amorphous $SiO_2$. When the bio-ceramic fibers 80 are warmed by placement adjacent to the body, the far infra-red emittance may increase, providing greater far infra-red treatment in the 8–14 micron wavelength range.

In order to provide a permeable barrier by which the bio-ceramic fibers 80 may be warmed by placement adjacent to the body and through which far infra-red (FIR) emittance may be made, apertured or foramenous MYLAR polyester or other plastic or resilient cover 90 may form a circular cover for the bio-ceramic fibers 80. The MYLAR may be sufficiently thick in order to properly retain the bio-ceramic fibers within the plastic case. The plastic case 52 may terminate on the bottom side adjacent to the apertured MYLAR 90 in a rim into which the circumference of the apertured MYLAR 90 fits. The apertures 92 may be evenly spaced across the surface of the apertured MYLAR 90.

Figure 10:
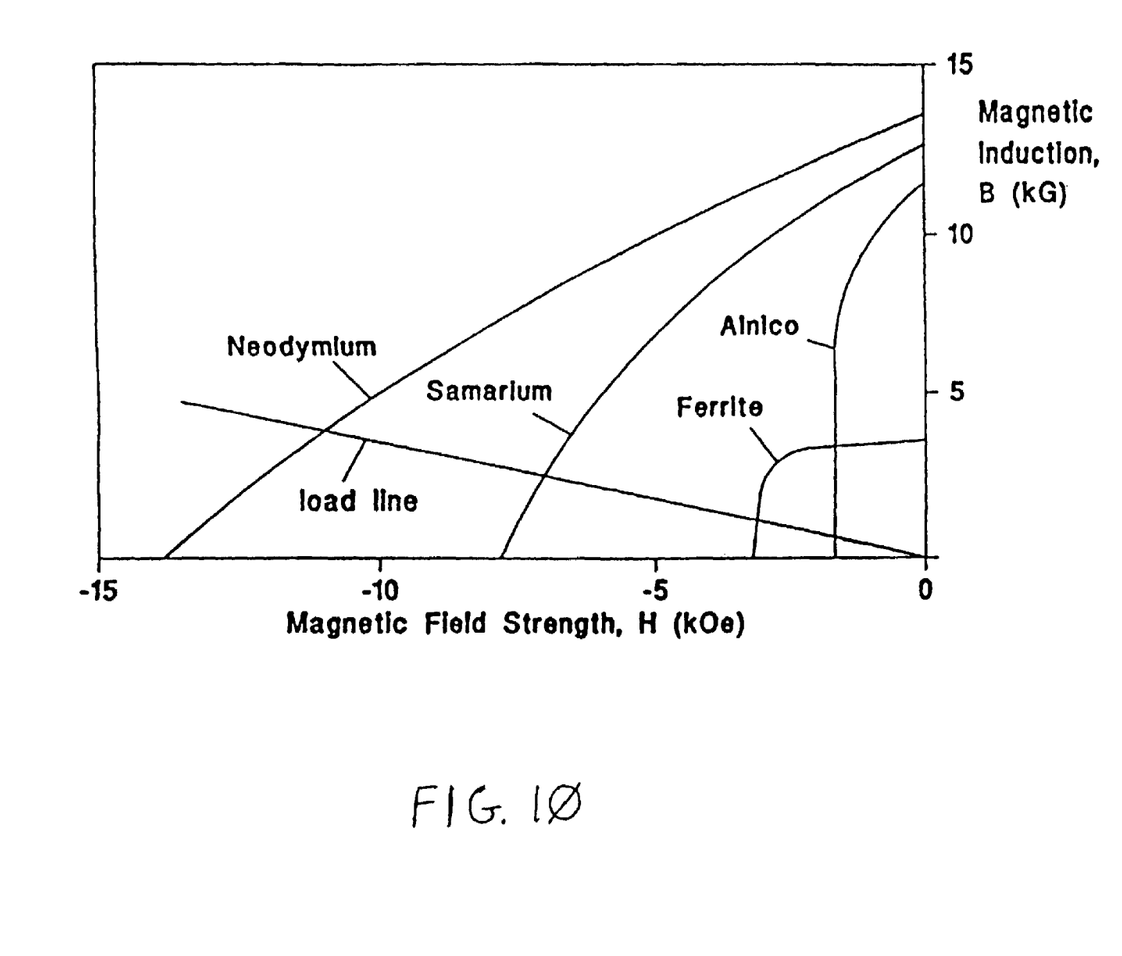
FIG. 10 shows a graph comparing the performance characteristics of neodymium, samarium, ferrite, and alnico magnets.

Neodymium (Nd) is currently preferred as the magnetic material used to constitute the strong magnet as its performance characteristics exceed those of samarium, ferrite, and alnico as can be seen in FIG. 10. In the graph shown in FIG. 10, the neodymium material provides the most powerful magnetic material. The load line on the graph in FIG. 10 indicates the maximum operational field and induction output of each material where the load line crosses the curve. Clearly, the neodymium magnet possesses the highest magnetic field output.

The present invention can provide a maximum field extension normal to its planar surface of approximately 3 inches with a field strength of 1.5 gauss at that distance. This is 6 times the field extension of a regular magnet known in the art. The maximum field strength at the surface of the present invention is in excess of 2000 gauss.

In order to enhance such magneto therapeutic properties, especially for iron or electrolytic fluids passing in proximity to such strong magnetic fields, FIGS. 5 through 9 show a variety of magnetic figurations to provide for alternating magnetic polarity as travel is made along the magnets of the present invention. By arranging for alternate polarity, changing magnetic fields are encountered by charged molecules or atoms passing sufficiently proximate to the magnetic joint wrap so as to be subject to its magnetic fields. It is known that such changing magnetic fields induce currents and will also serve to exert both repelling and attractive forces upon such charged molecules or atoms.

The stainless steel cap 60 provides electromagnetic strength to the side applied to the body (the apertured MYLAR 90 side). The stainless steel cap 60 also provides an aesthetically pleasing and highly polished mirror-like finish upon which a company logo or the like may be embossed.

In order to use the magnetotherapeutic device and the bio-ceramic fibers of the present invention, a pouch or band is used to place the device adjacent the skin. The heat from the body raises the temperature of the adjacent bio-ceramic fibers 80 through the apertured MYLAR 90 or otherwise. The bio-ceramic fibers 80 emit light in the far infra-red spectrum, preferably along the 8–14 micron wavelength range. The strong neodymium or other magnet 70 permeates the adjacent tissue with the available magnetic field, subjecting such tissue to magnetotherapy.

By providing a double-barreled approach whereby both magnetotherapy and far infra-red therapy are simultaneously provided, the present invention provides means by which better tissue therapy may be provided by both methods or treatment regimes. There may be some synergistic functions provided in the simultaneous application of both magnetotherapy, even strong magnetotherapy, and the far infra-red wave treatment.

While the present invention has been described with regards to particular embodiments, it is recognized that additional variations of the present invention may be devised without departing from the inventive concept.

What is claimed is:

1. A device for providing both magnetotherapy and far-infrared radiative treatment, comprising:
   a magnet, said magnet providing a magnetic field; and
   a far-infrared radiation emitter adjacent said magnet, said far-infrared radiation emitter emitting far-infrared radiation at body temperature;
   an insulating cover for holding said far-infrared emitter inside said insulating cover; and
   a polyester film shield having first and second sides, said polyester film shield adjacent said far-infrared emitter on said first side, said polyester film shield aiding in holding said far-infrared emitter inside said cover;
   whereby, simultaneous application of magnetotherapy and far-infrared radiative therapy occurs when the device is placed adjacent tissue to be treated.

2. The device for providing both magnetotherapy and far-infrared radiative treatment as set forth in claim 1, wherein said magnet further comprises:
   a strongly magnetic magnet incorporating or based on neodymium.

3. The device for providing both magnetotherapy and far-infrared radiative treatment as set forth in claim 1, wherein said far-infrared emitter further comprises:
   bio-ceramic fibers, said bio-ceramic fibers adjacent said magnet, said bio-ceramic fibers emitting far-infrared radiation (FIR).

4. The device for providing both magnetotherapy and far-infrared radiative treatment as set forth in claim 3, wherein said far-infrared emitter further comprises:
   bio-ceramic fibers woven into a mat.

5. The device for providing both magnetotherapy and far-infrared radiative treatment as set forth in claim 1, wherein said polyester film shield defines apertures or perforations to provide better communication between said far-infrared emitter on said first side of said polyester film shield and an area present on said second side of said polyester film shield across said polyester film shield.

6. The device for providing both magnetotherapy and far-infrared radiative treatment as set forth in claim 1, wherein said insulating cover comprises a plastic case holding said magnet and said far-infrared emitter in place with respect to one another and with respect to said plastic case.

7. The device for providing both magnetotherapy and far-infrared radiative treatment as set forth in claim 1, further comprising:
   a stainless steel plate, said stainless steel plate adjacent said magnet;
   whereby
   said magnetic field provided by said magnet is diminished on a side of said stainless steel plate opposite that of said magnet.

8. The device for providing both magnetotherapy and far-infrared radiative treatment as set forth in claim 7, wherein said magnetic field provided by said magnet is augmented on a side of said stainless steel plate the same as that of said magnet.

9. The device for providing both magnetotherapy and far-infrared radiative treatment as set forth in claim 1, further comprising a solid plate adjacent said magnet, wherein said solid plate is embossed with an emblem, design, or symbol.

10. The device for providing both magnetotherapy and far-infrared radiative treatment as set forth in claim 1 wherein said magnet has alternating magnetic polarity.

11. The device for providing both magnetotherapy and far-infrared radiative treatment as set forth in claim 10 wherein said magnet having alternating magnetic polarity comprises planar alternating magnetic means whereby travel in any direction along said magnet provides alternating magnetic polarity.

12. The device for providing both magnetotherapy and far-infrared radiative treatment as set forth in claim 11 wherein alternating magnetic polarity of said magnet is selected from the group consisting of:
    alternating magnetic triangles, alternating magnetic squares, and series of alternating concentric circles.

13. A device for providing both magnetotherapy and far-infrared radiative treatment, comprising:
    a plastic case, said plastic case open on one side and having a closed end;
    a stainless steel plate, said stainless steel plate adjacent said closed end of said plastic case and held within said plastic case;
    a strongly magnetic magnet based on or incorporating neodymium, said magnet adjacent said stainless steel plate and held within said plastic case, said magnet providing a magnetic field; and
    bio-ceramic fibers providing a far-infrared radiation emitter, said bio-ceramic fibers adjacent said magnet and emitting far-infrared radiation at body temperature, said bio-ceramic fibers held within said plastic case adjacent said magnet;
    whereby, simultaneous application of magnetotherapy and far-infrared radiative therapy occurs when the device is placed adjacent tissue to be treated.

14. The device for providing both magnetotherapy and far-infrared radiative treatment as set forth in claim 13, wherein said far-infrared emitter further comprises:
    said bio-ceramic fibers woven into a mat.

15. The device for providing both magnetotherapy and far-infrared radiative treatment as set forth in claim 13, further comprising:
    said magnetic field provided by said magnet is diminished on a side of said stainless steel plate opposite that of said magnet.

16. The device for providing both magnetotherapy and far-infrared radiative treatment as set forth in claim 13, further comprising:
    said magnetic field provided by said magnet is augmented on a side of said stainless steel plate the same as that of said magnet.

17. The device for providing both magnetotherapy and far-infrared radiative treatment as set forth in claim 13, further comprising:
    said stainless steel plate is embossed with an emblem, design, or symbol; and
    said plastic case being transparent and said embossment of said stainless steel plate is visible.

18. The device for providing both magnetotherapy and far-infrared radiative treatment as set forth in claim 13 wherein said magnet has alternating magnetic polarity.

19. The device for providing both magnetotherapy and far-infrared radiative treatment as set forth in claim 18 wherein said magnet having alternating magnetic polarity comprises planar alternating magnetic means whereby travel in any direction along said magnet provides alternating magnetic polarity.

20. The device for providing both magnetotherapy and for-infrared radiative treatment as set forth in claim 18 wherein alternating magnetic polarity of said magnet is selected from the group consisting of:

Alternating magnetic triangles, alternating magnetic squares, and series of alternating concentric circles.

21. A device for providing both magnetotherapy and far-infrared radiative treatment, comprising:

a magnet, said magnet providing a magnetic field; and a far-infrared radiation emitter adjacent said magnet, said far-infrared radiation emitter emitting far-infrared radiation at body temperature;

an insulating cover for holding said far-infrared emitter inside said insulating cover; and a stainless steel plate, said stainless steel plate adjacent said magnet so that said magnetic field provided by said magnet is diminished on a side of said stainless steel plate opposite that of said magnet;

whereby, simultaneous application of magnetotherapy and far-infrared radiative therapy occurs when the device is placed adjacent tissue to be treated.

22. A device for providing both magnetotherapy and far-infrared radiative treatment, comprising:

a magnet, said magnet providing a magnetic field; and a far-infrared radiation emitter adjacent said magnet, said far-infrared radiation emitter emitting far-infrared radiation at body temperature;

an insulating cover for holding said far-infrared emitter inside said insulating cover; and a solid plate adjacent said magnet, wherein said solid plate is embossed with an emblem, design, or symbol;

whereby, simultaneous application of magnetotherapy and far-infrared radiative therapy occurs when the device is placed adjacent tissue to be treated.

* * * * *